US010379128B2

(12) United States Patent
Yuan et al.

(10) Patent No.: US 10,379,128 B2
(45) Date of Patent: Aug. 13, 2019

(54) APPARATUS AND METHOD FOR ANALYZING BLOOD CLOTTING (71) Applicant: Medtronic, Inc., Minneapolis, MN (US)

(72) Inventors: Charlene Yuan, Brooklyn Park, MN (US); Trevor Huang, Maple Grove, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 257 days.

(21) Appl. No.: 13/868,598

(22) Filed: Apr. 23, 2013

(65) Prior Publication Data

US 2014/0315228 A1    Oct. 23, 2014

(51) Int. Cl.
*G01N 33/86*    (2006.01)
*G01N 33/49*    (2006.01)

(52) U.S. Cl.
CPC ......... *G01N 33/86* (2013.01); *G01N 33/4905* (2013.01)

(58) Field of Classification Search
CPC .. G01N 33/48; G01N 33/487; G01N 33/4875; G01N 33/49; G01N 33/4915; G01N 33/86; G01N 33/4905
See application file for complete search history.

(56) References Cited

U.S. PATENT DOCUMENTS

| | | | |
|---|---|---|---|
| 4,443,408 A * | 4/1984 | Mintz | 422/73 |
| 4,752,449 A | 6/1988 | Jackson et al. | |
| 5,174,961 A | 12/1992 | Smith | |
| 5,314,826 A | 5/1994 | Baugh | |
| 5,441,892 A | 8/1995 | Baugh | |
| 5,629,209 A | 5/1997 | Braun, Sr. et al. | |
| 5,925,319 A | 7/1999 | Baugh et al. | |
| 5,951,951 A | 9/1999 | Lane et al. | |
| 6,010,911 A | 1/2000 | Baugh et al. | |
| 6,221,672 B1 | 4/2001 | Baugh et al. | |
| 6,541,262 B1 | 4/2003 | Baugh et al. | |
| 6,613,286 B2 | 9/2003 | Braun, Sr. et al. | |
| 6,613,573 B1 | 9/2003 | Cohen | |
| 2003/0180824 A1* | 9/2003 | Mpock | C12Q 1/56 435/13 |
| 2004/0224416 A1* | 11/2004 | Ghai | G01N 33/86 436/8 |
| 2008/0268483 A1 | 10/2008 | Goldenberg et al. | |
| 2009/0130645 A1* | 5/2009 | Schubert | G01N 33/86 435/2 |
| 2012/0329082 A1 | 12/2012 | Viola et al. | |

FOREIGN PATENT DOCUMENTS

| | | |
|---|---|---|
| WO | WO1997/41444 | 11/1997 |
| WO | WO2000/40963 | 7/2000 |
| WO | WO2002/50535 | 6/2002 |
| WO | WO2005/106467 | 11/2005 |
| WO | WO 2006/067504 A2 | 6/2006 |
| WO | WO2009/073851 | 6/2009 |
| WO | WO2009/123555 | 10/2009 |

OTHER PUBLICATIONS

Breet et al., Comparison of Platelet Function Tests in Predicting Clinical Outcome in Patients Undergoing Coronary Stent Implantation, JAMA, Feb. 24, 2010, vol. 303, No. 8.
Eikelboom et al., "Antiplatelet Drugs: Antithrombotic Therapy and Prevention of Thrombosis, $9^{th}$ ed: American College of Chest Physicians Evidence-Based Clinical Practice Guidelines" Chest 2012; 141; e89S-e119S.
Gurbel et al., "Platelet Function Monitoring in Patients With Coronary Artery Disease" Journal of the American College of Cardiology, vol. 50, No. 19, 2007.
Hillman, Robert S. PhD "Letter to the Editor—Platelet Aspirin Resistance Detection and Validation" JACC, vol. 47, No. 12, 2006, Jun. 20, 2006: 2563-70.
Pakala et al., "Currently Available Methods for Platelet Function Analysis: Advantages and Disadvantages" Cardiovascular Revascularization Medicine 2010.
Picker, Susanne M. "In-Vitro Assessment of Platelet Function" Transfusion and Apheresis Science 44 (2011) 305-319.
Pittens et al., "Comparison Between Hirudin and Citrate in Monitoring the Inhibitory Effects of P2Y12 Receptor Antagonists With Different Platelet Function Test" Journal of Thrombosis and Haemostasis, 7: 1929-1949.
Weber et al., "A Point-of-Care Assessment of the Effects of Desmopressin on Impaired Platelet Function Using Multiple Electrode Whole-Blood Aggregometry in Patients After Cardiac Surgery" www.anesthesia-analgesia.org, Mar. 2010, vol. 110, No. 3.
PCT/US2014/020580, Partial International Search Report, dated Jun. 26, 2014.
PCT/US2014/032774, PCT International Search Report and Written Opinion, dated Jul. 17, 2014.

* cited by examiner

*Primary Examiner* — Renee Claytor
*Assistant Examiner* — Susan E. Fernandez (57) ABSTRACT Systems, apparatuses and methods include evaluation the clotting time or strength of clotting in the presence of various clot-affecting reagents to obtain a profile of clot analysis for determination of bleeding complications. The various reagents may be included in a single cartridge for use in a blood clotting analysis device.

16 Claims, 3 Drawing Sheets

APPARATUS AND METHOD FOR ANALYZING BLOOD CLOTTING

FIELD

This disclosure generally relates to, among other things, apparatuses and methods for detecting changes in a property of a fluid, such as clotting of blood.

BACKGROUND

A number of apparatuses for providing point-of-care analysis of blood clotting are available. These apparatuses are configured to provide valuable information regarding blood clotting, platelet function and bleeding complications. Such apparatuses are useful in a variety of circumstances such as before or during surgery to assist in determining or maintaining appropriate levels of anticoagulant therapy, or after surgery to determine blood status following discontinuation of anticoagulant therapy. However, additional or reconfigured apparatuses that provide for easy testing or additional information are desirable.

For example, easy, informative and accurate analysis of blood clotting and platelet function can be important for patients exhibiting abnormal bleeding post cardiopulmonary bypass. Although more than half of such patients exhibit abnormal bleeding due to incomplete surgical hemostasis, which is often corrected by exploration, a large number of such patients exhibit abnormal bleeding because of acquired platelet dysfunctions, consumptive coagulopathy, heparin rebound, protamine excess, primary fibrinolysis, etc. Accordingly, acquiring information regarding platelet function and bleeding complications could help to identify a cause of abnormal bleeding that is not a result of incomplete surgical hemostasis and reduce the reoperation rate.

SUMMARY

This disclosure describes, among other things, apparatuses, systems and methods that provide for ready and informative evaluation of blood clotting status. The methods, systems and apparatuses are, in embodiments, configured to allow testing of multiple aspects of clotting function, such as for example heparin rebound, protamine excess, consumptive coagulopathy, platelet dysfunction, primary fibrinolysis or the like, in a single apparatus. In embodiments, a single cartridge for use in a blood clotting analysis system includes multiple chambers housing different clot affecting reagents that may be combined with a patient's blood for clotting analysis. Clotting time or clot strength may be analyzed in the presence of the reagents in each chamber, or clotting times or clot strength in the presence of different reagents may be compared, to obtain a fuller spectrum of analysis than possible with previous systems and apparatuses.

As described herein, the selection of appropriate agents for use in combination with clotting time or clot strength analysis may provide a detailed understanding of blood clotting, platelet function and bleeding complications.

In embodiments, a method includes comparing activated clotting time in the presence and absence of heparinase to diagnose residual heparin or heparin rebound. The method further includes comparing activated clotting time in the presence and absence of heparin to diagnose protamine excess. The method further includes comparing clot strength in the presence of heparinase and presence or absence of a platelet activator, such as ADP, to diagnose platelet dysfunction. The method further includes comparing activated clotting time in the presence of heparinase and the presence or absence of plasma to diagnose comsumptive coagulopathy. The method further includes comparing activated clotting time and clot strength in the presence of heparinase and the presence or absence of fibrinogen, or an antifibrinolytic agent, such as Tranexamic acid, to diagnose fibrinogen deficiency, fibrin polymerization disorders or hyperfibrinolysis. Accordingly, embodiments of the methods described herein allow for analysis of residual heparin or heparin rebound, protamine excess, platelet dysfunction, comsumptive coagulopathy, and fibrinogen deficiency (due to hemodilution, blood losses and/or consumption), or fibrin polymerization disorder (induced by plasma expander), or hyperfibrinolysis.

In embodiments, systems are configured to carry out such methods or to allow one to carry out such methods. For example, a system configured to test activated clotting time and clot strength may include a number of chambers in which clotting time or strength may be tested. The chambers may include different reagents for purposes of evaluating different aspect of clotting. For example, a first chamber may contain kaolin (or other activator); a second chamber may contain kaolin (or other activator) and heparinase; a third chamber may contain kaolin (or other activator) and heparin; a fourth chamber may contain kaolin (or other activator), ADP (or other platelet activator), and heparinase; a fifth chamber may include kaolin (or other activator), plasma, and heparinase; and a sixth chamber may contain kaolin (or other activator), fibrinogen (or other fibrinolysis inhibiting agent), and heparinase. Clotting time, clot strength or both may be determined in each of the six chambers and results may be compared to gain a detailed understanding of blood clotting, platelet function and bleeding complications. For example, activated clotting time (ACT) in the first and second chambers may be compared to diagnose residual heparin or heparin rebound. ACT in the first and third chambers may be compared to diagnose protamine excess. Clot strength in the second and fourth chambers may be compared to diagnose platelet dysfunction. ACT in the second and fifth chambers may be compared to diagnose comsumptive coagulopathy. ACT, clot strength or both in the second and sixth chambers may be compared to diagnose fibrinolysis. The system preferably includes appropriate electronics (e.g., memory, processor, circuitry, etc.) to record clot time or clot strength parameters and compare such parameters among the results obtained from each chamber. The system may include a display to output results of clot times, clot strengths, or comparisons of clot time and strength among the various containers.

In embodiments, a cartridge for use in a blood clot analysis apparatus or system has a plurality of chambers. The chambers may be preloaded with reagents as described above; e.g., a first chamber contains kaolin (or other activator); a second chamber contains kaolin (or other activator) and heparinase; a third chamber contains kaolin (or other activator) and heparin; a fourth chamber contains kaolin (or other activator), ADP (or other platelet activator), and heparinase; a fifth chamber contains kaolin (or other activator), plasma, and heparinase; and a sixth chamber contains kaolin (or other activator), fibrinogen (or other fibrinolysis inhibiting agent), and heparinase. The chambers may be configured such that clotting analysis may be carried out in the chambers or may allow for the reagents to be introduced into a separate testing chamber for purposes of clotting analysis. Preferably, clotting analysis is performed in the reagent chambers.

One or more embodiments of the apparatuses, systems or methods described herein provide one or more advantages over prior apparatuses, systems or methods for evaluating a change in a property of a liquid, such as clotting of blood. For example, the apparatuses, systems and methods described herein may allow for bleeding complications to be identified following surgery, such as cardiopulmonary bypass, which may reduce reoperation rate to identify a potential source for bleeding. By way of example, if a post-surgical bleeding complication is identified using an apparatus, system or method described herein, a healthcare provide may choose to treat the bleeding complication or wait to see whether the complication passes before reoperating to determine whether a source of bleeding resulting from incomplete or improper surgical procedure or closure is the cause of the patient's bleeding. This and other advantages will be readily understood from the following detailed description.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description several specific embodiments of compounds, compositions, apparatuses, systems and methods are disclosed. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a composition, apparatus, system, method or the like, means that the components of the composition, apparatus, system, method or the like are limited to the enumerated components and any other components that do not materially affect the basic and novel characteristic(s) of the composition, apparatus, system, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

As used herein, determining or correlating "strength of clotting" means performing a calculation or estimation that employs a parameter indicative of clotting that occurs after activating clotting time or initiation of clot formation to determine or correlate the parameter to the strength of the clot.

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

As used herein, a "predetermined" threshold value is a value that is determined prior to the time in which it is compared to another value. The value may be based on baseline data obtained earlier in time than the value to which it is being compared, may be a value placed in memory prior to analysis, or the like.

This disclosure generally relates to, inter alia, apparatuses, systems and methods that provide for ready and informative evaluation of blood clotting status. The methods, systems and apparatuses are, in embodiments, configured to allow testing of multiple aspects of clotting function, such as for example heparin rebound, protamine excess, consumptive coagulopathy, platelet dysfunction, primary fibrinolysis or the like, in a single apparatus. In embodiments, a single cartridge for use in a blood clotting analysis system includes multiple chambers housing different clot affecting reagents that may be combined with a patient's blood for clotting analysis. Clotting time or clot strength may be analyzed in the presence of the reagents in each chamber, or clotting times or clot strength in the presence of different reagents may be compared, to obtain a fuller spectrum of analysis than possible with previous systems and apparatuses.

In embodiments, the methods described herein are employed by, or the systems described herein include, any suitable apparatus for analyzing blood clotting. For example, plunger-type systems or apparatuses such as those described in U.S. Pat. Nos. 6,010,911; 5,174,961; 4,752,449; 5,951,951; 5,925,319; 5,314,826; and 5,541,892; systems or apparatuses that employ ferromagnetic washers moved by electromagnets such as those described in U.S. Pat. Nos. 5,629,209 and 6,613,286; or the like may be employed in accordance with the teaching presented herein or may be modified to perform the methods described herein. Each of the afore-mentioned patents is hereby incorporated by reference in their respective entirety to the extent that it does not conflict with the disclosure presented herein. In aspects, the description presented herein is tailored to systems and apparatuses that employ ferromagnetic washers moved by electromagnets. However, it should be understood that other suitable systems and apparatuses, in many cases, may be used to carry out the methods described herein.

Regardless of the type of system employed, a blood clotting analysis system includes a chamber into which blood may be introduced for analysis. The system is typically configured to mix the blood with one or more reagent that may affect clotting of the blood. For example, the system may employ sonic, ultrasonic or other waves, washers, plungers, rods, shaking, or the like to mix the blood and one or more reagents. The reagents or agitation of blood may facilitate clotting of the blood. The system is configured to monitor changes in blood viscosity and correlate such changes with clotting status. For example, the system may include one or more detectors for monitoring waves, monitoring position or rate of movement of an object such as a plunger or washer, monitoring relative phase of a rod, or the like to determine whether blood viscosity or clotting status has changed. Typically, the system is configured to determine the amount of time for blood clotting to occur, which is often referred to as activated clotting time. The system may include more than one chamber configured to contain blood and different reagents that affect clotting so that comparisons of activating clotting time or clot strength in the various chambers can be used to derive information regarding the blood clotting process.

Figure 1:
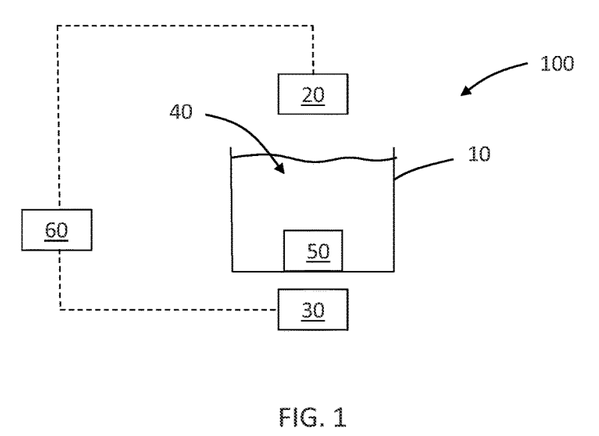
FIG. 1 is a schematic drawing of selected components of an embodiment of a blood analysis system.
Figure 2:
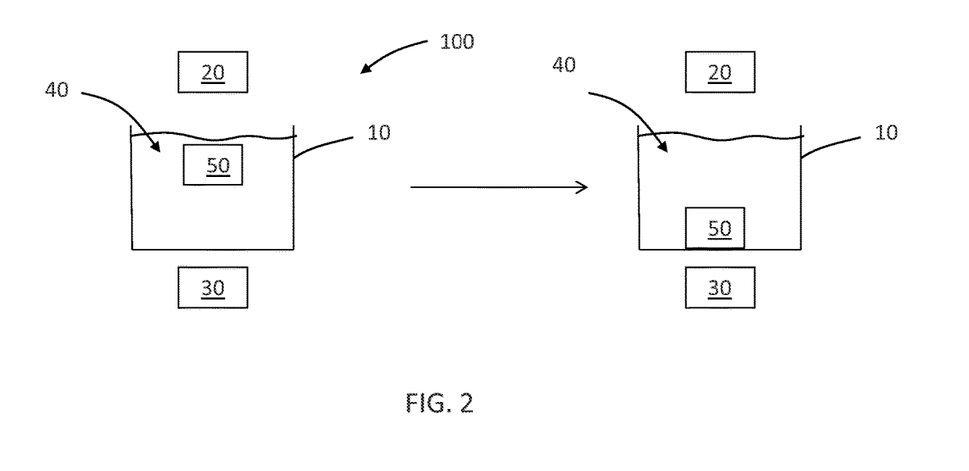
FIG. 2 is a schematic drawing of selected components of an embodiment of a blood analysis system showing an object moveable within a chamber containing blood.

By way of example and with reference to FIGS. 1-2, schematic drawings of selected components of an example of a blood analysis system 100 are shown. The depicted system 100 is system that employs a ferromagnetic object 50 movable within blood 40 contained within chamber 10. In embodiments, the chamber is configured to remain stationary during the testing process. The object 50 is moveable against gravity by electromagnet 20, which is operably coupled to electronics 60 (see, FIG. 2, left). Electronics 60 are configured to control activation of electromagnet 20. The object 50 may be moved against gravity and the position or rate of movement of the object 50 within the chamber 10 as object 50 falls through blood 40 may be detected by sensor 30 (see, FIG. 2, right), which is also operably coupled to electronics 60. In embodiments where multiple chambers are employed, the electronics 60 are preferably configured to independently move ferromagnetic objects 50 in each chamber 10 independently and without cross-talk. One or more detectors or sensors 30 may be employed to detect movement of the objects 50 within individual chambers or among chambers.

Electronics 60 may include a processor, memory, user interface, timer or counter, powers source or the like. Electronics may include any suitable processor, such as one or more microprocessors, DSPs, ASICs, FPGAs, programmable logic circuitry, or the like, and the functions attributed to the processor herein may be embodied as hardware, firmware, software or any combination thereof. Memory may store instructions that cause processor to provide the functionality ascribed to a system or apparatus described herein, and may store information used by processor to provide the functionality ascribed to a system or apparatus described herein. Memory may include any fixed or removable magnetic, optical, or electrical media, such as RAM, ROM, CD-ROM, hard or floppy magnetic disks, EEPROM, or the like. Memory may also include a removable memory portion that may be used to provide memory updates or increases in memory capacities. A power source may deliver operating power to components of a system or apparatus described herein. Power source may be an AC or DC power source, such as a battery and a power generation circuit to produce the operating power.

Still with reference to FIGS. 1-2, as blood 40 viscosity increases, such as when the blood clots, the rate of movement of object 50 falling through blood 40 will decrease. Electronics 60, based on data from sensor, are configured to determine the distance the object 50 falls or the velocity at which the object 50 falls. Electronics 60 may be configured to detect activated clotting times by, for example, determining when distance or velocity decreases by a predetermined amount or percent relative to an initial distance or velocity. As discussed above, additional details regarding such types of blood clotting analysis apparatuses and systems are described in, for example, U.S. Pat. Nos. 5,629,209 and 6,613,286.

As described in U.S. patent application Ser. No. 13/788,283, systems and apparatuses employing a moveable ferromagnetic object 50, such as a washer may be configured to evaluate the strength of clotting in addition to, or alternatively to, activated clotting time. U.S. patent application Ser. No. 13/788,283, filed on Mar. 7, 2013, entitled "Apparatus and Method for Analyzing Blood Clotting" is hereby incorporated herein by reference in its entirety to the extent that it does not conflict with the disclosure presented herein.

In embodiments, a single cartridge, which may be disposable, is used in a blood analysis system to assess a variety of aspects of blood clotting. The cartridge includes multiple chambers that may contain blood clotting affecting reagents. The reagent chambers may be chambers in which blood clotting analysis is performed or may be in communication with chambers in which the clotting analysis is performed, where reagents from the reagent chamber are delivered to (e.g., drawn into or flow into) the clotting chamber for analysis. The reagents and clotting analysis (e.g., clotting time or clot strength) are selected to allow for a broad assessment of bleeding diagnostics.

Figure 3:
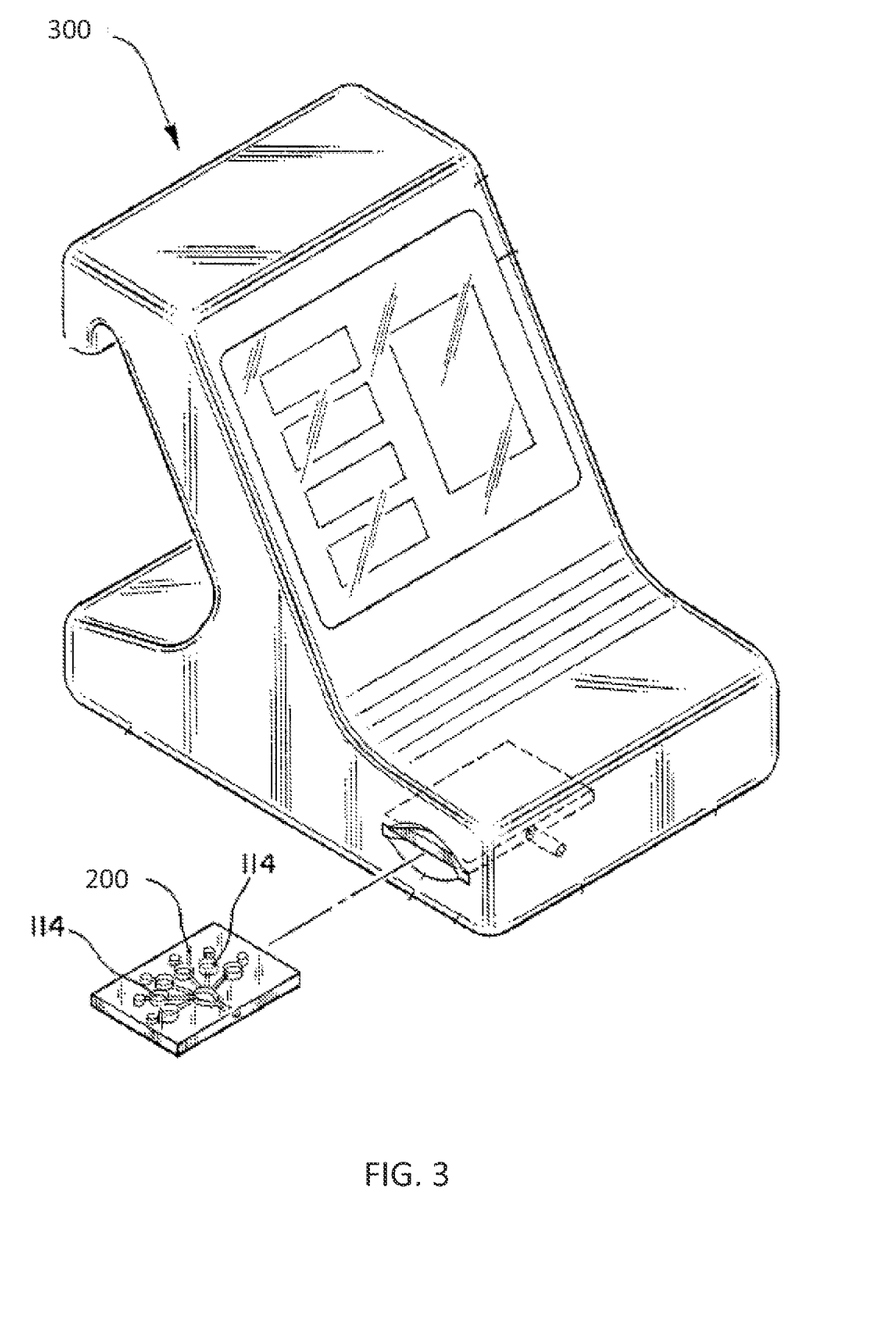
FIG. 3 is a schematic perspective view of an embodiment of a cartridge and a machine that may be used in accordance with the teachings presented herein.
Figure 4:
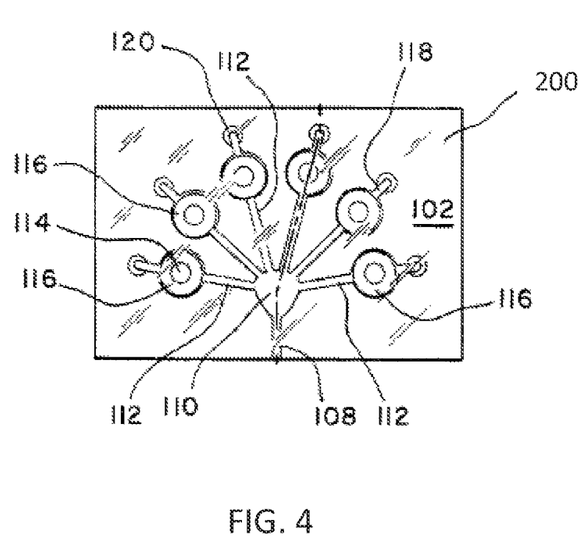
FIG. 4 is a schematic top plan view of an embodiment of a cartridge that may be used in accordance with the teachings presented herein.

Referring now to FIGS. 3-4 embodiments of a cartridge 200 and blood analyzer 300 are shown. Of course, cartridges and analyzers other than those depicted and described herein with regard to FIGS. 3-4 may be used or modified to be used in accordance with the teachings presented herein.

FIG. 3 depicts an embodiment of a disposable cartridge 200 and associated blood analysis device 300. The cartridge 200 and blood analyzer 300 comprise apparatus for detecting the viscosity of blood, measuring the elapsed time required for the viscosity to change (e.g., associated with activated clotting time or clot strength), and deriving and displaying that (and other information) concerning the clotting of the blood. In operation, the cartridge 200 may be inserted into the blood analyzer 300 before or after the cartridge is filled with the blood whose viscosity is to be tested. The depicted cartridge 200 includes a plurality of fluid-receiving chambers 114. The analyzer device 300 then conducts an analytical test following a predetermined procedure in accordance with the type of analysis desired. By use of the cartridge 200, the analyzer 300 accurately, reliably, and quickly conducts various tests, including, but not limited to, viscosity-related tests, for example, blood coagulation time tests, dose-response tests, and titration tests.

After a cartridge 200 containing a fluid sample is placed in the blood analyzer device 300, a ferromagnetic material such as the ferromagnetic washer 116 shown in FIG. 4 residing within a blood clotting analysis chamber 114 is raised through the fluid sample and allowed to drop. The analyzer device 300 then detects and measures the time required for the ferromagnetic material 116 to fall through the fluid sample. As the viscosity of the fluid changes (either increasing or decreasing), the fall time of the ferromagnetic material 116 through the fluid sample will change correspondingly. The device 300 is further able to distinguish the type of analytical test to be conducted and to compute the results of the test based on this determination. These test results may then be compared (for example, through computer-programmed comparisons) with other programmed test information or with other test results.

A top view of an embodiment of a cartridge 200 is shown in greater detail in FIG. 4. The depicted cartridge 200 is substantially planar and formed of a rigid substantially integral material, for example, a plastic such as PETG (polyethylene terephthalate), that is, most preferably, inert with respect to the fluid sample being tested. The rigid material from which the cartridge 200 is formed may be partially or wholly transparent. The cartridge 200 may be manufactured as a unitary or monolithic piece (for example, by injection molding techniques), or the cartridge 200 may be assembled from various separate parts. In embodiments, a separate and distinct top (not shown) is attached to the cartridge 200 after a viscosity-altering substance (e.g. blood clot affecting reagent) is placed in the cartridge 200. In embodiments, the top is a heat sealable polyester film material such as Melinex®.

In the depicted embodiment, an injection port 108 is provided in a nominal front portion of the cartridge 200 for admission of the fluid sample into the cartridge 200. The injection port 108 directs the fluid sample into a fluid receiving/dispensing reservoir 110. From the fluid receiving/dispensing reservoir 110 the fluid proceeds through one or more conduits 112 to each conduit's respective blood clotting analysis chamber 114. The motive force for this movement of the fluid through the cartridge 200 is provided by a fluid injection or pumping mechanism, for example, a manually activated syringe, or by other methods, such as by suction, for example, a vacuum system. Most preferably, each blood clotting analysis chamber 114 is equidistant from the fluid receiving/dispensing reservoir 110, so that the fluid moves from the fluid receiving/dispensing reservoir 110 simultaneously or nearly so into each blood clotting analysis chamber 114. Each blood clotting analysis chamber 114 preferably has a volume of about 100 microliters to about 250 microliters. Although six fluid-receiving chambers 114 are shown in FIG. 4, it should be understood that any desired number of blood clotting analysis chambers 114 in any desired orientation can be formed in the cartridge 200. Cartridges with other orientations, configurations, numbers, and sizes of any such blood clotting analysis chamber 114 are contemplated herein.

Preferably, the multiple blood clotting analysis chambers 114 are filled nearly simultaneously to ensure accuracy of the analytical test results. Such simultaneous or near-simultaneous filling may be accomplished by providing the fluid receiving/dispensing reservoir 110 is with a substantially triangular configuration so that it acts as a uniform manifold to deliver the fluid to the blood clotting analysis chambers 114.

Air contained in the cartridge 200 may be vented from the cartridge 200 as the fluid sample enters. In the depicted embodiment, a second conduit 118 leads from the blood clotting analysis chamber 114 to an air vent/fluid plug device (not shown). As the fluid sample enters the cartridge 200 and moves into any given blood clotting analysis chamber 114, air contained in the fluid receiving/dispensing reservoir 110, first conduit 112, and blood clotting analysis chamber 114 is vented through the second conduit 118 and out of the cartridge 200.

One or more reagents may be mixed with blood in, or prior to entry to, a blood clotting analysis chamber 114. The reagents may be placed in appropriate reagent chambers of the cartridge prior to completing assembly of the cartridge (e.g., securing the top to the cartridge). The reagent chambers may be the blood clotting analysis chambers 114 or may be a chamber (not shown) in the path of a conduit 112 between the fluid receiving/dispensing reservoir 110 and a blood clotting analysis chamber 114. The reagents are preferably dried, lyophilized, or the like to extend the shelf life of the cartridges that contain the reagents.

In embodiments, one or more reagent chambers of a cartridge contain a clotting rate enhancing agent. In embodiments, all of the reagent chambers include a clotting rate enhancing agent. As used herein, a clotting rate enhancing agent is a contact pathway (also known as intrinsic pathway) activator or a tissue factor pathway (also known as extrinsic pathway), or a combination of both. Examples of contact pathway activators include kaolin, celite, silica, ellagic acid, phospholipids, etc. In the presence of a clotting rate enhancing agent, such as kaolin, clotting time is referred to as "activated clotting time" or "ACT", which is typically substantially less than without such an agent. Tissue factor is also called thromboplastin (factor III). In the presence of clotting rate enhancing agent, such as tissue factor, clotting time is referred to as "Prothrombin Time" or "PT". PT time is substantially less than ACT.

In embodiments, one or more reagent chambers contain a heaprin neutralizer. Heparin neutralizers include agents that inhibit the function of heparin and include polyprene, heparinase, and heparin antagonists such as protamine. By way of example, heparinase inactivates or enzymatically breaks down heparin, which is an anticoagulant often used in surgeries, such as open heart surgery, to prevent clotting. Excess heparin or heparin rebound (where previously bound, and thus unavailable, heparin becomes free and is available to act as an anticoagulant) is a common cause of post-surgical bleeding. If clotting time of the test chamber contains heparinase (or another heparin neutralizer) decreases compared to the test chamber without heparinase (or other heparin neutralizer), excessive heparin could be identified as possible cause of post-surgical bleeding.

Accordingly, patients are typically administered an agent that counteracts the effects of heparin (e.g., heparin antagonist) following surgeries in which the patient was administered heparin before or during surgery. One such agent is protamine. For purposes of this disclosure, "protamine" also refers to protamine sulfate. However, protamine itself is a weak anticoagulant. If excess protamine is administered, the protamine, which is intended to prevent the anticoagulant effects of heparin, can be a cause of post-surgical bleeding. To test to see whether excess protamine may be the cause of bleeding, one or more reagent chambers may contain low level of heparin. If clotting time decreases in the presence of low level of heparin, excess protamine may be determined to be a contributing factor to post-surgical bleeding. The excess protamine may be also confirmed by little or no clotting time change between chambers with and without heparin neutralizer, such as heparinase. The other purpose of chambers with heparin is to assess the platelet and fibrin contribution to the clot strength with thrombin activity inhibited by heparin. This can be achieved by comparison of clot strength between the chamber without heparin (e.g., chamber with heparin neutralizer) and chamber with heparin.

In embodiments, one or more reagent chambers contain a platelet activator. Platelet activators may be used to diagnose platelet dysfunction. If clot time decreases or clot strength increases in the presence of a platelet activator, the platelets may be determined to be functioning normally. However, if clot strength or clotting time is not changed (or changed below a threshold amount), platelet dysfunction may be a factor contributing to abnormal patient bleeding. Alternatively, platelet inhibitors can also be used to assess platelet function. If clot time increases or clot strength decreases in the presence of a platelet inhibitor, the platelets may be determined to be functioning normally. If no changes or changes below a threshold amount, platelet dysfunction may be a factor contributing to bleeding.

Examples of platelet activators that may be used include collagen, adenosine diphosphate (ADP), epinephrine, arachidonic acid.

Without intending to be bound by theory, it is believed that, in some scenarios, clotting time may not be greatly affected by the presence of platelet activators and thus, platelet dysfunction may not readily be identified through the use of clot time parameters. However, in some of such scenarios, it is believed that clot strength may vary substantially with the presence (or absence) of platelet activators (when there is not platelet dysfunction). Accordingly, if no or little change in clot strength is observed in the presence of a platelet activator, a determination that platelet dysfunction may be a contributing factor to bleeding may be made.

In embodiments, one or more reagent chambers contain fibrinogen or a fibrinolysis inhibiting agent. As used herein, a "fibrinolysis inhibiting agent" is an agent that inhibits the breakdown or degradation of fibrin. Examples of fibrinolysis inhibiting agents include inhibitors of plasmin or plasminogen (which includes inhibitors of the conversion of plasminogen to plasmin), such as tranexamic acid, epsilon amino caproic acid (AMICAR), aprotinin, plasminogen activator inhibitor 1, plasminogen activator inhibitor 2, $\alpha_2$-antiplasmin, and $\alpha_2$-macroglobulin, etc. For diagnosis of bleeding caused by fibrinogen deficiency or fibrin polymerization disorder, fibrinogen is a preferred agent. For diagnosis of bleeding caused by hyperfibrinolysis, an antifibrinolytic drug, such as tranexamic acid, is a preferred agent. In the reaction chamber with fibrinogen, the clot strength is expected to be stronger compared to the reaction chamber without fibrinogen if bleeding is caused by weak fibrin polymerization. The clotting time may be decreased or not change as a result of added fibrinogen depends on the clotting time threshold setting. In embodiments, a chamber containing fibrinogen also contains a platelet inhibitor to evaluate the effect of fibrin or fibrinogen on clotting in the absence of (or reduced) effect from platelets.

If hyperfibrinolysis is the cause of bleeding, the reaction chamber with an antifibrinolytic agent will have delayed fibrinolysis time and the clot strength will be stronger in the fibrinolysis process. Little to no change in clotting time is expected.

In embodiments, one or more reagent chambers include plasma. In some patients, consumptive coagulopathy causes clotting factors to be depleted and thus unavailable for clotting of surgical wounds. Plasma can be used to contribute depleted factors. Accordingly, if clot strength increases (e.g. by a predetermined amount or percentage) or clot time decreases (e.g. by a predetermined amount or percentage) in the presence of plasma, consumptive coagulopathy may be considered to be a factor contributing to post-surgical bleeding.

The reagents listed above are only examples of those that may be used or employed in cartridges as described herein. It will be understood that other agents may be employed. Examples of reagents that may be employed are presented in Tables 1-3 below.

TABLE 1

Platelet function test with platelet activators to test platelet adhesion/aggregation

| Platelet Activators | Drug Monitored | Function of Activator | Function of Drug |
|---|---|---|---|
| Collagen/ADP | Clopidrogrel | Activate P2Y1 and P2Y2 receptors | Inhibit P2Y1 and P2Y2 linked pathways |
| Collagen/epinephrine | Aspirin (ASA) | Activate COX-1 pathway | Inhibit COX-1 pathway |
| Arachidonic acid | Asprin (ASA) | Activate COX-1 pathway | |

TABLE 2

Platelet Inhibitors

| Platelet Inhibitors | Drug Monitored | Function of Drug |
|---|---|---|
| GPIIb/IIIa inhibitor | Abciximab Tirofiban Eptifbatide | Inhibit platelet activation by block GPIIb/IIIa receptors |
| ADP-induced platelet aggregation inhibitor | Thienopyridines Clopidogrel Ticlopidine Prasugrel | Inhibit PY21 and P2Y2 linked pathways |
| COX activity inhibitor | Aspirin (ASA) | Inhibitor of COX pathway activity |
| Cyclic AMP inhibitor | Dipyridamole Cilostazol | |

TABLE 3

Selected reagents for use in test chamber

| Reagent | Rationale for Use |
|---|---|
| Heparin neutralizing agent (e.g., heparinase, polybrene, or protamine) | To remove heparin effect. |
| Heparin | Inhibits thrombin allowing the contribution of fibrin and platelets to be assessed. Or to remove the protamine effect. |
| Activators (e.g., Celite, Kaolin, Tissue Factor) | Increase speed of clotting allowing faster results. |
| Glycoprotein IIb/IIIa inhibitors, | Inhibit platelet function allowing the contribution of fibrinogen to be assessed. |
| Collagen and/or ADP, epinephrine | Activated platelets via P2Y1 and P2Y2 receptors. Clopidogrel and other thienopyridines inhibit P2Y12 ACP receptor. |
| Arachidonic acid | Activates platelets via the production of thromboxane A2 |
| Fibrinogen | To promote fibrin formation and assess fibrin polymerization |
| Activator (Reptilase and Factor XIIIa) | Activates fibrin formation without affecting platelets |
| Antifibrinolytic drugs (e.g., Tranexamic acid) | Reverse fibrinolysis |

In embodiments, one or more combinations of one or more reagents are included in one or more chamber.

In Table 4 a specific embodiment is presented as an example of a system that has six different channels or chambers in which different combinations of agents are mixed with blood and various aspects of blood clotting are determined and compared to provide for thorough analysis of platelet function and bleeding complications. The reagents in Table 4 can be replaced with, supplement with, etc. other reagents listed in Table 1, 2 and 3. For example, to further speed of clotting process, the activator kaolin can be replaced with Tissue Factor; heparin neutralizing agent can be polybrene instead of heparinase; etc.

TABLE 4

Agents in various channels and comparisons that can be made for diagnosis

| Channel | Reagent | Diagnosis |
| --- | --- | --- |
| 1 | Kaolin | |
| 2 | Kaolin/ Heparinase | Compare activated clotting time (ACT) of channels 1 and 2 to diagnose residual heparin/heparin rebound. |
| 3 | Kaolin/Heparin | Compare ACT of channels 1, 2 and 3 to diagnose protamine excess. Compare clot strength of channel 2 and 3 to assess platelet and fibrin contribution. |
| 4 | Kaolin/ADP/ Heparinase | Compare clot strength of channels 2 and 4 to diagnose platelet dysfunction. |
| 5 | Kaolin/Plasma/ Heparinase | Compare ACT of channels 2 and 5 to diagnose consumptive coagulopathy. |
| 6 | Kaolin/ Fibrinogen/ Platelet inhibitor | Compare ACT and clot strength of channels 1 and 6 to assess fibrin polymerization without contribution from platelet. |

As indicated in Table 4, data regarding activated clotting time, clot strength, fibrinolysis, etc. obtained from a given chamber having one or more agents that affect blood clotting may be compared with similar data obtained from another chamber in which different agents are mixed with blood.

It will be understood that blood clotting analysis as described herein may be performed with the use of more than one cartridge or without any cartridges, cut with different separate reaction chambers. However, the use of a single cartridge provides for an easy to use and convenient blood diagnostic analysis.

Methods described in this disclosure, including those attributed to apparatuses or systems, or various constituent components, may be implemented, at least in part, in hardware, software, firmware or any combination thereof. For example, various aspects of the methods may be implemented within one or more processors, including one or more microprocessors, DSPs, ASICs, FPGAs, or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

Such hardware, software, firmware may be implemented within the same apparatus or within separate apparatuses to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, apparatuses and methods described in this disclosure may be embodied as instructions on a computer-readable medium such as RAM, ROM, NVRAM, EEPROM, FLASH memory, magnetic data storage media, optical data storage media, or the like. Such computer-readable medium is non-transitory. The instructions may be executed by one or more processors to support one or more aspects of the functionality described in this disclosure.

A number of embodiments of methods, apparatuses, and systems are described herein. A summary of selected aspects of methods, devices and systems described herein is provided below.

In a first aspect, a cartridge for use in a blood clotting analyzer includes a plurality of reagent chambers configured to serve as blood clotting analysis chambers or in communication with blood clotting analysis chambers when used with the blood clotting analyzer. The plurality of reagent chambers comprises: (i) a first chamber housing a clotting rate enhancing agent; (ii) a second chamber housing a clotting rate enhancing agent and a heparin neutralizer; (iii) a third chamber housing a clotting rate enhancing agent, a platelet activator, and a heparin neutralizer; and (iv) comprises a fourth chamber housing a clotting rate enhancing agent, fibrinogen, and a platelet inhibitor.

A second aspect is a cartridge of the first aspect, wherein the plurality of reagent chambers further comprises a fifth chamber housing a clotting rate enhancing agent and heparin.

A third aspect is a cartridge of the first or second aspects, wherein the plurality of reagent chambers further comprises a sixth chamber housing a clotting rate enhancing agent, plasma, and a heparin neutralizer.

A fourth aspect is a cartridge according to any one of the preceding aspects, wherein the plurality of reagent chambers further comprises a seventh chamber housing a clotting rate enhancing agent, a fibrinolysis inhibiting agent, and a heparin neutralizer.

A fifth aspect is a cartridge according to the fourth aspect, wherein the fibrinolysis inhibiting agent is selected from the group consisting of an inhibitor of plasmin or plasminogen.

A sixth aspect is a cartridge according to the fifth aspect, wherein the fibrinolysis inhibiting agent is selected from the group consisting of plasminogen activator inhibitor 1, plasminogen activator inhibitor 2, $\alpha_2$-antiplasmin, and $\alpha_2$-macroglobulin.

A seventh aspect is a cartridge according to any one of the preceding aspects, wherein the plurality of reagent chambers further comprises an eighth chamber housing a clotting rate enhancing agent, a platelet inhibitor, and a heparin neutralizer.

An eighth aspect is a cartridge according to any one of the preceding aspects, wherein the clotting rate enhancing agent in each of the chambers is the same and is selected from the group consisting of celite, kaolin, and tissue factor.

A ninth aspect is a cartridge according to the eighth aspect, wherein the clotting rate enhancing agent is kaolin.

A tenth aspect is a cartridge according to any one of the preceding aspects, wherein the platelet activator is selected from the group consisting of collagen, epinephrine, adenosine diphosphate (ADP), and arachidonic acid.

An eleventh aspect is a cartridge according to the tenth aspect, wherein the platelet activator is ADP.

A twelfth aspect is a cartridge according to any of the preceding aspects, wherein the platelet inhibitor is a glycoprotein IIb/IIIa inhibitor.

A thirteenth aspect is a cartridge according to any one of the preceding aspects, wherein heparin neutralizer is heparinase.

A fourteenth aspect is a cartridge according to any one of the preceding aspects, wherein the reagent chambers configured to serve as blood clotting analysis chambers and wherein the cartridge further comprises a plurality of ferromagnetic objects, wherein at least one of the plurality of ferromagnetic objects is disposed within each of the plurality of reagent chambers.

eleventh fifteenth aspect is a blood clotting analysis system comprising (i) a cartridge according to any one of aspects 1-14; and (ii) a blood clotting analyzer configured to receive the cartridge and mix the reagents from the reagent chambers with blood in blood analysis chambers. The blood clotting analyzer comprises: (i) one or more detectors configured to monitor a parameter associated with blood clotting; and (ii) electronics operably coupled to the one or more detectors, wherein the electronics are configured to determine clotting time or clotting strength based on data received from the detector and to compare clotting time or clotting strength from different blood analysis chambers in which different reagents are mixed with the blood.

A sixteenth aspect is a system according to the fifteenth aspect, wherein the cartridge is a cartridge according to the fourteenth aspect and wherein system further comprises one or more electromagnets operably coupled to the electronics. The electronics are configured to activate the one or more electromagnet to cause the ferromagnetic object to move.

A seventeenth aspect is a system according to the sixteenth aspect, wherein the electronics are configured to activate the one or more electromagnetics to independently move the ferromagnetic objects in each of the plurality of blood analysis chambers (preferably with little or no crosstalk).

An eighteenth aspect is a system according to any one of aspects 15-17, wherein the electronics are configured to compare activated clotting time of blood mixed with reagents from the first chamber to activated clotting time of blood mixed with reagents from the second chamber.

A nineteenth aspect is a system according to any one of aspects 15-18, wherein the electronics are configured to compare clot strength of blood mixed with reagents from the second chamber to clot strength of blood mixed with reagents from the third chamber.

A twentieth aspect is a system according to any one of aspects 15-19, wherein the electronics are configured to compare clotting time of blood mixed with reagents from the first chamber to clotting time of blood mixed with reagents from the fourth chamber.

A twenty-first aspect is a system according to any one of aspects 15-20, wherein the electronics are configured to compare clot strength of blood mixed with reagents from the first chamber to clot strength of blood mixed with reagents from the fourth chamber.

A twenty-second aspect is a system according to any one of aspects 15-21, wherein the electronics are configured to compare: (i) clotting time of blood mixed with reagents from the first chamber to clotting time of blood mixed with reagents from the fifth chamber; (ii) clotting time of blood mixed with reagents from the second chamber to clotting time of blood mixed with reagents from the fifth chamber; or (iii) clotting time of blood mixed with reagents from the first chamber to clotting time of blood mixed with reagents from the second chamber and to clotting time of blood mixed with reagents from the fifth chamber.

A twenty-third aspect is a system according to any one of aspects 15-22, wherein the electronics are configured to compare clot strength of blood mixed with reagents from the second chamber to clot strength of blood mixed with reagents from the fifth chamber.

A twenty-fourth aspect is a system according to any one of aspects 15-23, wherein the electronics are configured to compare clotting time, clot strength or fibrinolysis time of blood mixed with reagents from the first chamber to activated clotting time, clot strength or fibrinolysis time of blood mixed with reagents from the sixth chamber.

A twenty-fifth aspect is a system according to any one of aspects 15-24, wherein the electronics are configured to compare clot time or clot strength of blood mixed with reagents mixed from the second chamber with clot time or clot strength of blood mixed with reagents from the seventh chamber.

A twenty-sixth aspect is a system according to any one of aspects 15-25, wherein the electronics are configured to compare: (i) clot strength of blood mixed with reagents mixed from the second chamber with clot strength of blood mixed with reagents from the eighth channel; (ii) clot strength of blood mixed with reagents mixed from the third chamber with clot strength of blood mixed with reagents from the eighth channel; or (iii) clot strength of blood mixed with reagents mixed from the second chamber with clot strength of blood mixed with reagents from the third chamber and clot strength of blood mixed with reagents from the eighth chamber.

A twenty-seventh aspect is a method comprising: (i) mixing a patient's blood with a clotting rate enhancing agent in a first chamber of a blood clotting analysis system and determining clotting time of the blood within the first chamber; (ii) mixing a patient's blood with a clotting rate enhancing agent and a heparin neutralizer in a second chamber of the blood clotting analysis system and determining clotting time and clot strength of the blood in the second chamber; (iii) mixing a patient's blood with a clotting rate enhancing agent, a platelet activator, and a heparin neutralizer in a third chamber of the blood clotting analysis system and determining clot strength of the blood within the third chamber; (iv) mixing a patient's blood with a clotting rate enhancing agent, fibrinogen and a platelet inhibitor in a fourth chamber of the blood clotting analysis system and determining clotting time and clot strength of the blood in the fourth chamber; (v) comparing the clotting time of the blood in the first chamber with the clotting time of the blood in the second chamber; (vi) comparing the clot strength of the blood in the second chamber with the clot strength of the blood in the third chamber; and (vii) comparing the clotting time of the blood in the first chamber with the clotting time of the blood in the fourth chamber.

A twenty-eighth aspect is a method according to the twenty-seventh aspect, further comprising: (i) mixing a patient's blood with a clotting rate enhancing agent and heparin in a fifth chamber of the blood clotting analysis system and determining clotting time of the blood in the fifth chamber; and (ii) comparing the clotting time of the blood in the second chamber with the activated clotting time of the blood in the fifth chamber.

A twenty-ninth aspect is a method according to the twenty-seventh or twenty-eighth aspects, further comprising: (i) mixing a patient's blood with a clotting rate enhancing agent, plasma, and a heparin neutralizer in a sixth chamber of the blood clotting analysis system and determining clotting time of the blood in the sixth chamber; and (ii) comparing the clotting time of the blood in the second chamber with the clotting time of the blood in the sixth chamber.

A thirtieth aspect is a method according to any one of aspects 27-29, further comprising: (i) mixing a patient's blood with a clotting rate enhancing agent, fibrinolysis inhibiting agent, and a heparin neutralizer in a seventh chamber of the blood clotting analysis system and determining clotting time or clot strength of the blood in the seventh chamber; and (ii) comparing clot time or clot strength of blood mixed with reagents mixed from the second chamber with clot time or clot strength of blood mixed with reagents from the seventh chamber.

A thirty-first aspect is a method according to any one of aspects 27-30, further comprising: (A) mixing a patient's blood with a clotting rate enhancing agent, a platelet inhibitor, and a heparin neutralizer in a eighth chamber of the blood clotting analysis system and determining clot strength of the blood in the eighth chamber; and (B) comparing (i) clot strength of blood mixed with reagents mixed from the second chamber with clot strength of blood mixed with reagents from the eighth chamber; (ii) clot strength of blood mixed with reagents mixed from the third chamber with clot strength of blood mixed with reagents from the eighth chamber; or (iii) clot strength of blood mixed with reagents mixed from the second chamber with clot strength of blood mixed with reagents from the third chamber and clot strength of blood mixed with reagents from the eighth chamber. A thirty-second aspect is a method according to any one of aspects 27-31, wherein the method is carried out by the blood clotting analysis system.

Thus, embodiments of APPARATUS AND METHOD FOR ANALYZING BLOOD CLOTTING are disclosed. One skilled in the art will appreciate that the apparatuses, systems and methods described herein can be practiced with embodiments other than those disclosed. The disclosed embodiments are presented for purposes of illustration and not limitation. One will also understand that components of the leads depicted and described with regard the figures and embodiments herein may be interchangeable.

Use of "first," "second," "third," etc. in the description above and the claims that follow is not intended to necessarily indicate that the enumerated number of objects are present. For example, a "seventh" chamber is merely intended to differentiate from another chamber (such as a "first" or "second" chamber) and does not necessarily mean that seven or more chambers are present.

The invention claimed is:

1. A cartridge for use in a blood clotting analyzer, comprising a plurality of reagent chambers configured to serve as blood clotting analysis chambers or in communication with blood clotting analysis chambers when used with the blood clotting analyzer, wherein the plurality of reagent chambers comprises:
   a first chamber containing a clotting rate enhancing agent but not containing a heparin neutralizer, a platelet activator, or fibrinogen;
   a second chamber containing a clotting rate enhancing agent and a heparin neutralizer but not containing a platelet activator or fibrinogen;
   a third chamber containing a clotting rate enhancing agent, a platelet activator, and a heparin neutralizer but not containing fibrinogen;
   a fourth chamber containing a clotting rate enhancing agent, fibrinogen, and a platelet inhibitor;
   a fifth chamber containing a clotting rate enhancing agent, plasma, and a heparin neutralizer prior to addition of the sample of blood to be tested; and
   an optional sixth chamber containing a clotting rate enhancing agent and heparin.

2. A cartridge according to claim 1, wherein the plurality of reagent chambers further comprises an additional chamber containing a clotting rate enhancing agent, a fibrinolysis inhibiting agent, and a heparin neutralizer.

3. A cartridge according to claim 1, wherein the plurality of reagent chambers further comprises an additional chamber containing a clotting rate enhancing agent, a platelet inhibitor, and a heparin neutralizer.

4. A cartridge according to claim 1, wherein the reagent chambers are configured to serve as blood clotting analysis chambers and wherein the cartridge further comprises a plurality of ferromagnetic objects, wherein each of the plurality of reagent chambers has at least one of the plurality of ferromagnetic objects disposed therein.

5. A cartridge according to claim 1,
   wherein the first chamber contains the clotting rate enhancing agent prior to addition of a sample of blood to be tested;
   wherein the second chamber contains the clotting rate enhancing agent and the heparin neutralizer prior to addition of the sample of blood to be tested;
   wherein the third chamber contains the clotting rate enhancing agent, the platelet activator, and the heparin neutralizer prior to addition of the sample of blood to be tested; and
   wherein the fourth chamber contains the clotting rate enhancing agent, fibrinogen, and the platelet inhibitor prior to addition of the sample of blood to be tested.

6. A cartridge according to claim 1, wherein the first, second, third, and fourth chambers do not contain blood.

7. A cartridge according to claim 1, wherein the fifth chamber does not contain blood.

8. A blood clotting analysis system comprising:
   a cartridge according to claim 1; and
   a blood clotting analyzer configured to receive the cartridge and mix the reagents from the reagent chambers with blood in blood analysis chambers, the blood clotting analyzer comprising:
   one or more detectors configured to monitor a parameter associated with blood clotting; and
   electronics operably coupled to the one or more detectors, wherein the electronics are configured to determine clotting time or clotting strength based on data received from the one or more detectors and to compare clotting time or clotting strength from different blood analysis chambers in which different reagents are mixed with the blood.

9. A system according to claim 8,
   wherein the reagent chambers of the cartridge are configured to serve as blood clotting analysis chambers and wherein the cartridge further comprises a plurality of ferromagnetic objects,
   wherein each of the plurality of reagent chambers has at least one of the plurality of ferromagnetic objects disposed therein,
   wherein the system further comprises one or more electromagnets operably coupled to the electronics, and
   wherein the electronics are configured to activate the one or more electromagnets to cause the ferromagnetic objects to move.

10. A system according to claim 9, wherein the electronics are configured to activate the one or more electromagnets to independently move the ferromagnetic objects in each of the plurality of blood clotting analysis chambers.

11. A system according to claim 9, wherein the electronics are configured to compare clotting time of blood mixed with reagents from the first chamber to clotting time of blood mixed with reagents from the second chamber.

12. A system according to claim 9, wherein the electronics are configured to compare clot strength of blood mixed with reagents from the second chamber to clot strength of blood mixed with reagents from the third chamber.

13. A system according to claim 9, wherein the electronics are configured to compare clotting time of blood mixed with reagents from the first chamber to clotting time of blood mixed with reagents from the fourth chamber.

14. A system according to claim 9, wherein the electronics are configured to compare clot strength of blood mixed with reagents from the first chamber to clot strength of blood mixed with reagents from the fourth chamber.

15. A cartridge for use in a blood clotting analyzer, comprising a plurality of reagent chambers configured to serve as blood clotting analysis chambers or in communication with blood clotting analysis chambers when used with the blood clotting analyzer, wherein the plurality of reagent chambers comprises:
  a first chamber containing a clotting rate enhancing agent but not containing a heparin neutralizer, a platelet activator, or fibrinogen;
  a second chamber containing a clotting rate enhancing agent and a heparin neutralizer but not containing a platelet activator or fibrinogen;
  a third chamber containing a clotting rate enhancing agent, a platelet activator, and a heparin neutralizer but not containing fibrinogen;
  a fourth chamber containing a clotting rate enhancing agent, fibrinogen, and a platelet inhibitor;
  a fifth chamber containing a clotting rate enhancing agent and heparin; a
  a sixth chamber containing a clotting rate enhancing agent, plasma, and a heparin neutralizer;
  a seventh chamber containing a clotting rate enhancing agent, a fibrinolysis inhibiting agent, and a heparin neutralizer; and
  an eighth chamber containing a clotting rate enhancing agent, a platelet inhibitor, and a heparin neutralizer,
  wherein the first chamber contains the clotting rate enhancing agent prior to addition of a sample of blood to be tested,
  wherein the second chamber contains the clotting rate enhancing agent and the heparin neutralizer prior to addition of the sample of blood to be tested,
  wherein the third chamber contains the clotting rate enhancing agent, the platelet activator, and the heparin neutralizer prior to addition of the sample of blood to be tested,
  wherein the fourth chamber contains the clotting rate enhancing agent, fibrinogen, and the platelet inhibitor prior to addition of the sample of blood to be tested,
  wherein the fifth chamber contains the clotting rate enhancing agent and heparin prior to addition of the sample of blood to be tested,
  wherein the sixth chamber contains the clotting rate enhancing agent, plasma, and the heparin neutralizer prior to addition of the sample of blood to be tested,
  wherein the seventh chamber contains the clotting rate enhancing agent, the fibrinolysis inhibiting agent, and the heparin neutralizer prior to addition of the sample of blood to be tested, and
  wherein the eighth chamber contains the clotting rate enhancing agent, the platelet inhibitor, and the heparin neutralizer prior to addition of the sample of blood to be tested.

16. A cartridge according to claim 15, wherein the first, second, third, fourth, fifth, sixth, seventh, and eighth chambers do not contain blood.

* * * * *